United States Patent [19]

Hofstetter et al.

[11] Patent Number: 5,569,193
[45] Date of Patent: Oct. 29, 1996

[54] SYRINGE SYSTEM ACCOMMODATING SEPARATELY STORABLE PREFILLED CONTAINERS FOR TWO CONSTITUENTS

[75] Inventors: John M. Hofstetter, Vernon Hills; John A. O'Neil, Mundelein; Richard W. Grabenkort, Barrington, all of Ill.

[73] Assignee: Abbott Laboratories, Abbott Park, Ill.

[21] Appl. No.: 408,463

[22] Filed: Mar. 22, 1995

[51] Int. Cl.[6] ............................................. A61M 37/00
[52] U.S. Cl. ...................................... 604/89; 604/91
[58] Field of Search ............................ 604/87–92, 191, 604/187, 232, 218

[56] References Cited

U.S. PATENT DOCUMENTS

| | | | |
|---|---|---|---|
| 3,477,432 | 11/1969 | Shaw | 604/91 |
| 4,957,637 | 9/1990 | Cornell | 604/89 X |
| 5,088,996 | 2/1992 | Kopfer et al. | 604/87 X |
| 5,158,546 | 10/1992 | Haber et al. | 604/87 |
| 5,372,586 | 12/1994 | Haber et al. | 604/89 |

Primary Examiner—John D. Yasko
Attorney, Agent, or Firm—A. Nicholas Trausch

[57] ABSTRACT

A prefilled, two-constituent system is provided with first and second containers. The first container includes a first chamber having a dispensing end. The dispensing end defines a dispensing passage communicating through the dispensing end to accommodate the dispensing of fluid from the first chamber. A movable seal is slidably disposed in the first chamber, and a first constituent is provided in the first chamber between the dispensing end and the seal. A second container includes a barrel that is sized to be disposed in the first container and that has a discharge end defining a discharge passage communicating through the discharge end to accommodate the discharge of fluid from the barrel. A plunger is slidably disposed within the barrel. A liquid second constituent is provided in the barrel between the discharge end and the plunger. The first container seal and the second container barrel discharge ends are engageable to cooperatively define a coupling accommodating the flow of the liquid second constituent from the second container barrel into the first chamber of the first container as the barrel moves outwardly relative to the first chamber.

18 Claims, 3 Drawing Sheets

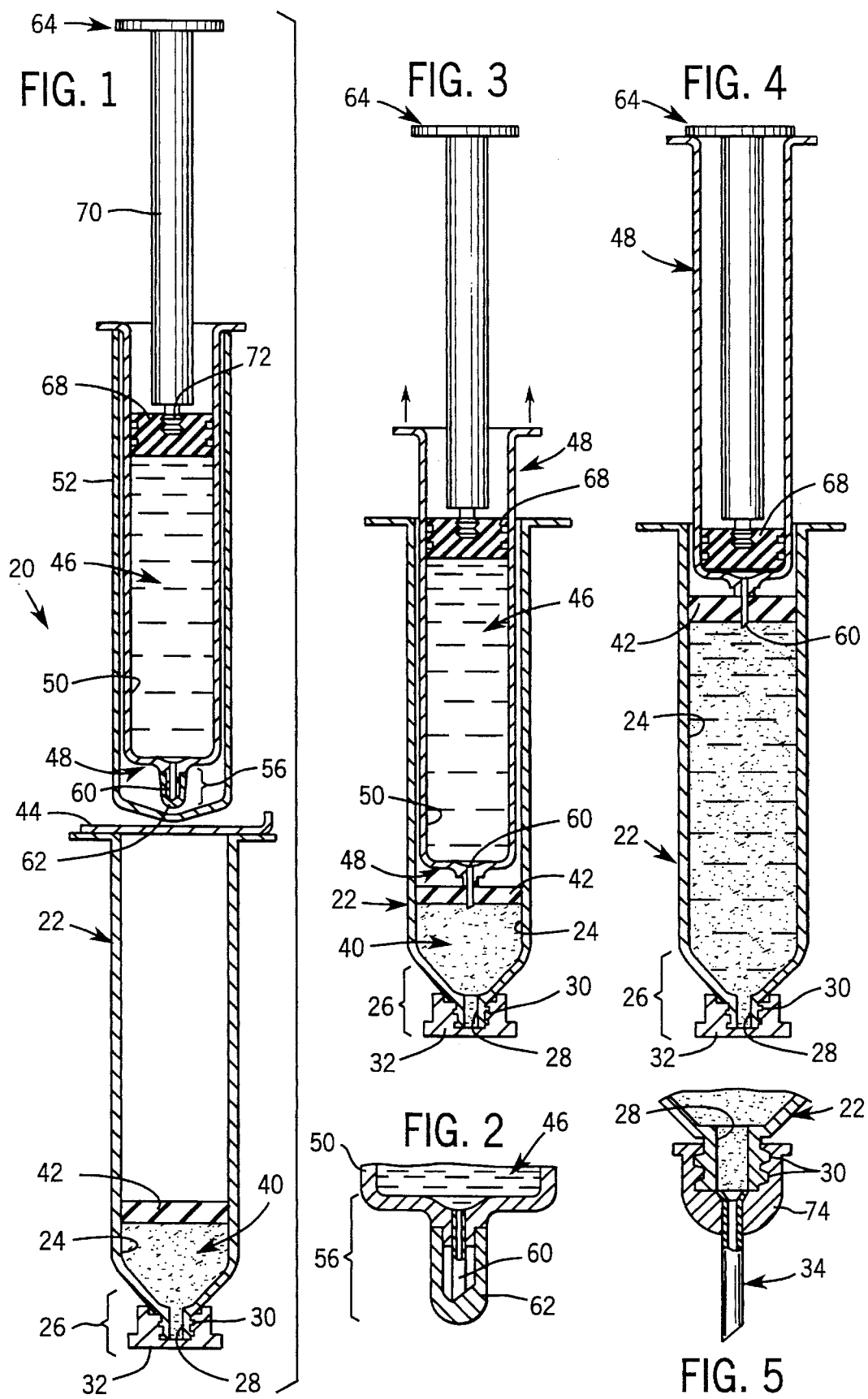

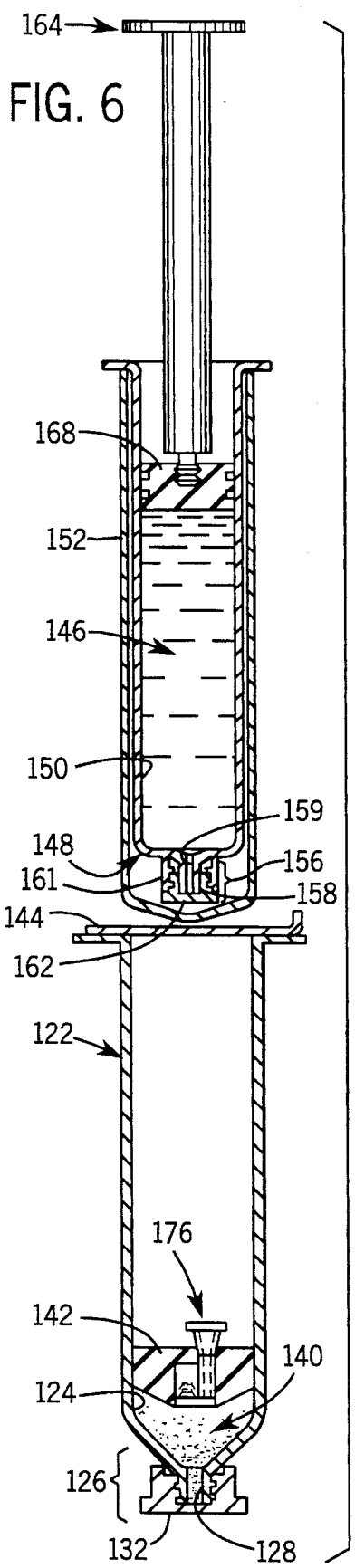
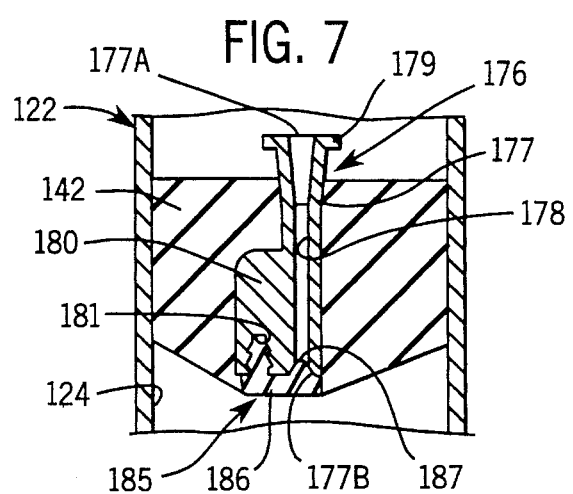
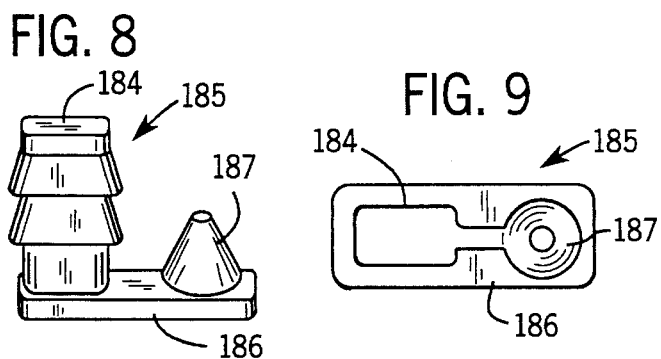
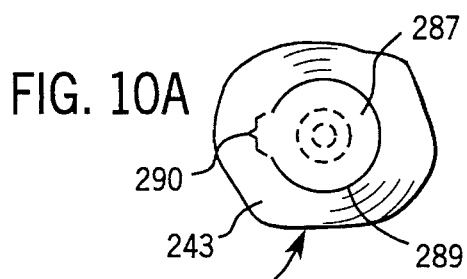
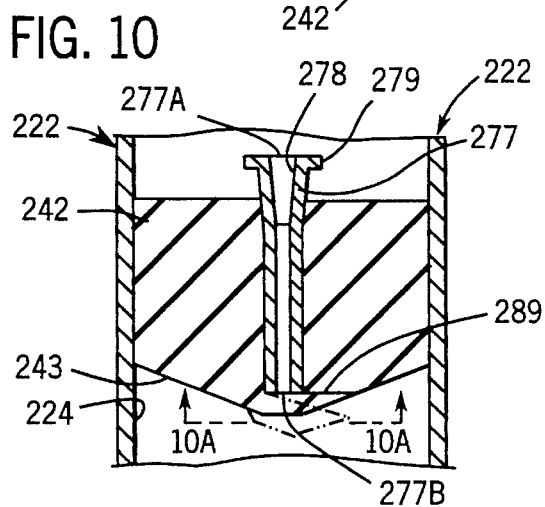

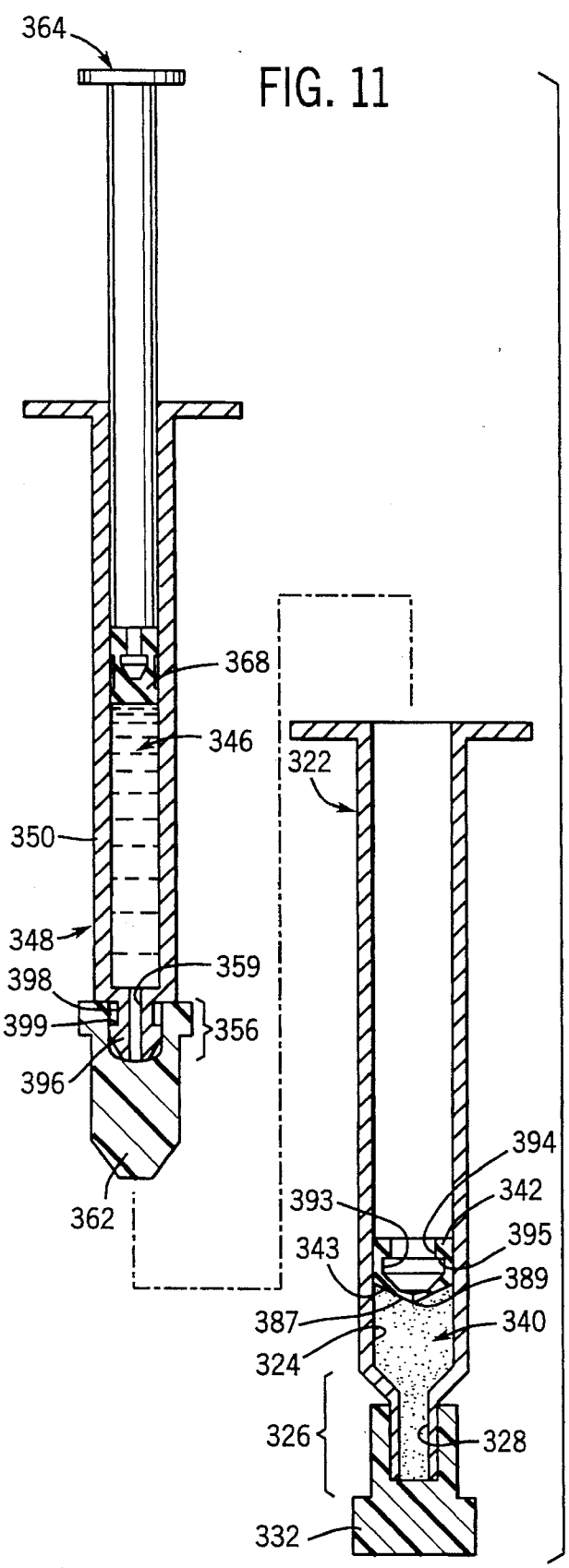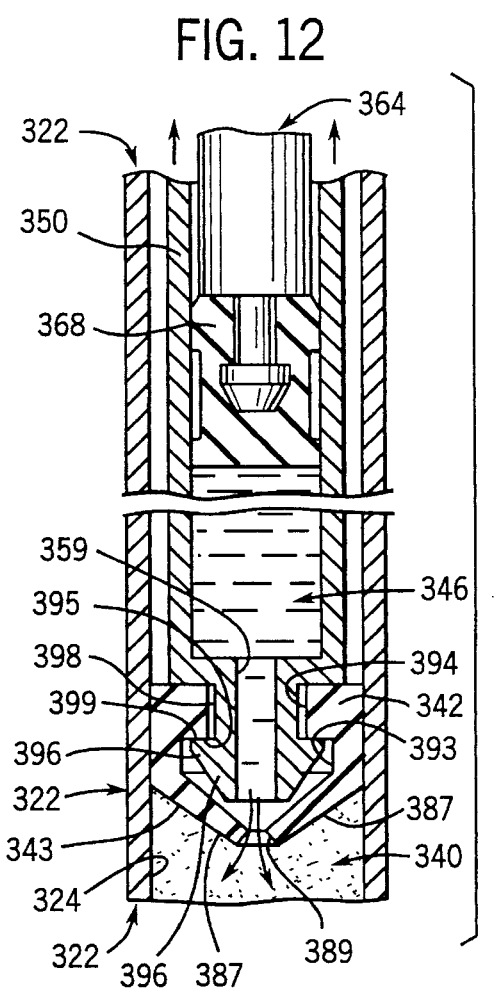

5,569,193

SYRINGE SYSTEM ACCOMMODATING SEPARATELY STORABLE PREFILLED CONTAINERS FOR TWO CONSTITUENTS

TECHNICAL FIELD

This invention relates to a packaging system and dispensing system for two constituents or components that are stored separately in isolation from each other but which must be combined or mixed together prior to dispensing. The invention is particularly suitable for use with a medicament, such as a drug in powder form, which must be dissolved and diluted in a liquid.

BACKGROUND OF THE INVENTION AND TECHNICAL PROBLEMS POSED BY THE PRIOR ART

In some medical applications, as well as in some industrial or other applications, it is necessary, or at least preferable, to maintain two components or constituents in isolation prior to combining the two components for subsequent dispensing as a solution, mixture, or other combination.

For example, some pharmaceutical preparations, such as injectable solutions or suspensions of a drug, are not sufficiently stable to accommodate prolonged storage prior to use. However, the components of the solution or suspension may have adequate stability if the components are stored separately prior to being combined.

It would be desirable to provide an improved system that will accommodate the packaging of two such components in isolation from each other, but which can be subsequently operated to combine or mix the components for dispensing. In particular, it would be advantageous to provide such an improved system with the capability, where necessary, for employing component containers that can be manufactured and/or stored separately as well as together.

It would be especially advantageous if such an improved system could be employed with two liquid components as well as with at least one solid component.

It would be desirable with such a system to positively seal both components from the ambient atmosphere as well as from each other.

It would also be beneficial if such an improved system could be provided in a self-contained form that is compact, portable, simple to manipulate, and readily adaptable to different proportions and dosages of the components.

Additionally, it would be desirable if such an improved system could readily accommodate the storage and administration of a variety of drugs which require reconstitution and/or dilution including, among other types, a medicament in powder form requiring mixing with a diluent, a medicament in liquid form requiring mixing with a diluent, and a lyophilized compound requiring mixing with a diluent.

The present invention provides an improved packaging and dispensing system which can accommodate designs having the above-discussed benefits and features.

SUMMARY OF THE INVENTION

The present invention provides a syringe system for storing two components or constituents in isolation from each other. The system can be subsequently operated for combining or mixing the two constituents and for then dispensing the combination.

The syringe system includes first and second containers. The first container includes a first chamber which has a dispensing end.

The dispensing end defines a dispensing passage communicating through the dispensing end to accommodate the dispensing of fluid from the first chamber. Preferably, a first removable closure is provided to occlude the dispensing passage.

A moveable seal is slidably disposed in the first chamber. The first chamber is preferably prefilled with a first constituent between the seal and the dispensing end.

The second container includes a barrel that is sized to be disposed in the first container and that has a discharge end defining a discharge passage communicating through the discharge end to accommodate the discharge of fluid front the barrel. Preferably, a second removable closure is provided to occlude the discharge passage.

A plunger is slidably disposed within the barrel. The second container is preferably prefilled with a liquid second constituent in the barrel between the discharge end and the plunger.

In order to combine the two constituents, the second closure, if any, is first removed from the barrel discharge end. The first container seal and the second container barrel discharge end are engageable to cooperatively define a coupling accommodating the flow of the liquid second constituent front the barrel into the first chamber as the second container and seal move outwardly relative to the first chamber. The liquid constituent is then moved (i.e., pushed or drawn) from the second container into the first container where the liquid second constituent mixes with the first constituent. The assembly may be shaken to promote mixing.

Subsequently, the first closure can be removed from the first container. Then the plunger, which is now engaged with the raised bottom of the second container, can be pushed inwardly. This carries both the second container and coupled seal further inwardly into the first chamber. This dispenses the mixed contents of the first chamber through the dispensing passage.

Numerous other advantages and features of the present invention will become readily apparent from the following detailed description of the invention, from the claims, and from the accompanying drawings.

BRIEF DESCRIPTION OF THE DRAWINGS

In the accompanying drawings that form part of the specification, and in which like numerals are employed to designate like parts throughout the same, FIG. 1 is a partial cross-sectional view of first embodiment of the syringe system of the present invention showing the first and second containers before they are coupled together;

FIG. 2 is a greatly enlarged, fragmentary, cross-sectional view of the discharge end of the second container;

FIG. 3 is a view of the components of FIG. 1 in an assembled condition with the seal in the first container penetrated by the piercing needle of the second container just prior to the second container being moved outwardly relative to the first container;

FIG. 4 is a view similar to FIG. 3, but FIG. 4 shows the second container moved outwardly relative to the first container to the maximum extent;

FIG. 5 is a greatly enlarged, fragmentary, cross-sectional view of the dispensing end of the first container shown with the first closure removed and replaced with a needle;

FIG. 6 is a cross-sectional view of a second embodiment of the present invention with the first and second containers separated prior to assembly;

FIG. 7 is a greatly enlarged, fragmentary, cross-sectional view of the seal of the first container of the second embodiment;

FIG. 8 is a perspective view of the valve member employed in the second embodiment seal;

FIG. 9 is a top plan view of the valve member shown in FIG. 8;

FIG. 10 is a view similar to FIG. 7, but FIG. 10 shows a modified seal of a third embodiment of the present invention;

FIG. 10A is a fragmentary, bottom plan view taken along the plane 10A—10A in FIG. 10;

FIG. 11 is a cross-sectional view of a fourth embodiment of the present invention showing the first and second containers separated prior to assembly; and FIG. 12 is a greatly enlarged, fragmentary, cross-sectional view of a portion of the assembled components of the fourth embodiment operated to open the mixing valve.

DESCRIPTION OF THE PREFERRED EMBODIMENT

While this invention is susceptible of embodiment in many different forms, this specification and the accompanying drawings disclose only some specific forms as examples of the invention. The invention is not intended to be limited to the embodiments so described, however. The scope of the invention is pointed out in the appended claims.

Figures illustrating the apparatus show some mechanical elements that are known and that will be recognized by one skilled in the art. The detailed descriptions of such elements are not necessary to an understanding of the invention, and accordingly, are herein presented only to the degree necessary to facilitate an understanding of the novel features of the present invention.

A first embodiment of the prefilled syringe system of the present invention is illustrated in FIGS. 1–5 and is designated generally therein by the reference number 20. The system includes a first container 22 defining a first chamber 24 and a dispensing end 26 defining a dispensing passage 28 communicating through the dispensing end 26 to accommodate the dispensing of fluid from the first chamber 24. It is presently contemplated that in the preferred embodiment the container 22 may be fabricated from a synthetic polymer, such as a thermoplastic material.

Preferably, the dispensing end 26 defines an exterior thread form 30 for receiving a threaded cap or first closure 32 and for subsequently receiving, upon removal of the closure 32, a hollow needle 34. Any other suitable conventional or special capping system may be employed.

A first component or constituent 40 is provided in the first container 22. The constituent 40, in the preferred contemplated embodiment for use in medical applications, can be a drug or other medicament in granular form, powder form, or other particulate form. It may also be a liquid. It is contemplated that the constituent 20 in the container 22 would typically be a drug which, if in solid form, requires reconstitution, or if in liquid form, requires dilution. Thus, the system of the present invention will be useful in the containment of hazardous drugs such as are used in oncological applications or in biotechnology delivery applications.

A movable seal 42 is slidably disposed in the first chamber 24 above the first constituent 40. Preferably, the seal is fabricated from a resilient, elastomeric material. In the preferred form, the seal 42 has an uncompressed diameter somewhat larger than the diameter of the chamber 24. A friction-fit engagement is established between the seal 42 and the chamber 24 that is sufficient to hold the seal 42 in place on top of the constituent 40 during normal packaging, shipping and handling. However, the force of engagement is sufficiently low to permit sliding of the seal 42 along the chamber 24 when the seal 42 is subjected to a sufficiently high axial force as described in detail hereinafter.

Also, as illustrated in FIG. 1, it is preferred to provide an outer seal or cover 44 over the upper, open end of the container 22. This prevents ingress of contaminants. The cover 44 may be an adhesive backed, flexible web that can be readily pulled off just prior to use of the system.

A second constituent 46, in the form of a liquid, is sealed within a second container 48. The liquid constituent 46 would typically be a diluent for diluting and/or reconstituting the first constituent 40. The second container 48 may be formed from the same synthetic polymer materials as used for the first container 22.

The second container includes a barrel 50 that is sized to be disposed in the first container 22 (FIGS. 3 and 4). Initially, in the pre-assembled condition, the second container 48 is preferably encased in a protective sleeve 52 which must be removed prior to use. The second container 48 also includes a plunger 64 which is slidably disposed within the second container barrel 50. The plunger 64 includes a piston 68 slidably received within the second container barrel 50.

The piston 68 is preferably initially located in contact with the liquid second constituent 46 at the upper end of the second container 48 as illustrated in FIG. 1. For packaging convenience, the plunger 64 may be provided with a shank 70 having a threaded end or snap-fit end 72 for engaging a mating thread form or snap-fit form in the top of the piston 68. Such a structure permits packaging of the system components with the plunger shank 70 not initially connected or assembled with the piston 68. When it is subsequently desired to use the system, the user can thread or snap-fit the shank 70 into the piston 68.

The second container barrel 50 has a discharge end 56 defining a discharge passage communicating through the discharge end to accommodate the discharge of fluid from the barrel 50. In the first embodiment illustrated in FIGS. 1–5, the second container barrel discharge passage is defined by the hollow interior of a piercing needle 60 which is mounted in the discharge end of the barrel 50.

Preferably, the second container 48 is initially provided to the user with a second cap or closure mounted to the second container barrel discharge end over the piercing needle 60 as shown in FIG. 2. The second closure 62 may be held on the discharge end of the second container by means of a snap-fit (or by other means, e.g., a threaded engagement (not illustrated) or the like). The operation of the packaging system syringe 10 will next be described with reference to the sequential operational steps illustrated in FIGS. 3–5. The first stage of the operation is illustrated in FIG. 2.

Just prior to use, the second closure 62 is removed to expose the piercing needle 60. Preferably, before the second closure 62 is removed, the second container 48 is inverted (so that the piercing needle 60 is pointing generally upwardly). This will ensure that the liquid constituent 46 cannot drip out. However, even if the second container 48 is not inverted, the liquid constituent 46 will not drip out. This is because the second container has no vent system that would admit ambient air into the second container 48 so as to permit the liquid constituent to flow out through the needle 60 solely under the influence of gravity. Absent such venting, the liquid constituent 46 remains in the second container 48 and is not able to flow out through the piercing needle 60.

With the second container 48 preferably inverted to point the piercing needle 60 upwardly, the first container 22 is inverted and aligned with the second container 48. Then relative movement is effected so as to locate the distal end of the second container 48 in the first container 22. As illustrated in FIG. 3, the second container 48 is inserted into the first container 22 until the piercing needle 60 engages, and penetrates completely through, the first container seal 42.

Before and during the step of inserting the second container 48 inside the first container 22, the plunger 64 is not moved relative to the second container 48. The plunger 64 remains in the initial, outermost orientation. After the two containers are telescopically disposed with the piercing needle 60 fully penetrating the second container seal 42, the plunger 64 is pushed inwardly within the second container 48. This causes the liquid second constituent 46 to flow out through the hollow piercing needle 60 into the first constituent 40 within the first chamber 24. The hydraulic pressure within the first chamber 24 acts on the second container seal 42 and the abutting distal end of the second container 48. This moves (i.e., pushes) the second container 48 outwardly relative to the first container 22. It will be appreciated that the ambient atmospheric pressure bears on the outside surface of the plunger piston 68, and this is effective in aiding the discharge of the liquid second constituent 46 into the first chamber 24.

When the piston 68 is seated at the bottom, discharge end of the second container 48, the top of the second container 48 is adjacent the top of the plunger 64. Substantially all of the liquid second constituent has been discharged through the hollow piercing needle 60 into the first chamber 24 of the first container where it forms a solution with, mixes with, or is otherwise combined with the first constituent 40. The assembly can be shaken to ensure good mixing.

After the constituents are sufficiently mixed, the first closure 32 is removed from the first container 22, and the dispensing end 36 can be connected to the receiving component or discharge tubing (not illustrated). Typically, a hollow needle 34 is mounted at the distal end of the first container dispensing end. The needle 34 may be of a conventional, single-ended type with a straight, hollow, stainless steel shaft, typically 20 gauge in size. The needle 34 may be provided with a swaged or molded hub 74 (FIG. 5) for engagement with the bottom, distal end of the first container dispensing end 36.

When properly mounted on the first container 22, the needle 34 is in alignment with the dispensing passage 28, and fluid communication is established between the dispensing passage 28 and the needle 34. After the needle 34 is properly mounted on the first container 22, (or after the first container is otherwise properly connected to some suitable receiving component), the plunger 64 and container 48 can be depressed by applying an axial force. This causes the combined constituents in the first chamber 24 to be dispensed or expelled from the chamber 24 through the needle 34.

It will be appreciated that the central portion of the first container seal 42 and the second container piercing needle 60 cooperatively define a connection means or coupling which accommodates the flow of the liquid second constituent from the second container into the first chamber of the first container. This connection or coupling accommodates the movement of the seal 42 together with the second container 48-first outwardly to move (i.e., push or draw) the liquid second constituent 46 into the first chamber, and subsequently inwardly into the first chamber to dispense the combined constituents.

An alternate embodiment of the syringe system of the present invention is illustrated in FIG. 6-9. Elements in the alternate embodiment which are the same as, or which function in an analogous manner to, elements of the first embodiment illustrated in FIGS. 1–5 are designated with three digit reference numbers wherein the last two digits are the same as the two digits of the reference number of the corresponding element in the first embodiment.

With reference to FIG. 6, the second embodiment of the syringe system includes a first container 122 and a second container 148. The first container 122 has an open upper end which is initially sealed with a removable cover 144. The first container 122 defines a first chamber 124 which contains a first constituent 140. The first constituent 140 is deposited in the bottom of the first container 122 which defines a dispensing end 126 having a dispensing passage 128 communicating through the dispensing end 126 to accommodate the dispensing of fluid from the first chamber 124. Normally, a first removable closure 132 is provided on the dispensing end 126. Suitable conventional or special cap retention systems may be provided, such as the mating thread forms as illustrated, snap-fit beads and grooves, etc.

A movable seal 142 is slidably disposed in the first chamber 124. The seal 142 is retained with sufficient frictional engagement to prevent its movement within the first container 122 during normal storage, transport, and handling.

As can be seen in FIG. 7, a novel conduit assembly 176 is mounted in the seal 142. The conduit assembly 176 includes a generally elongate conduit 177 extending through the seal 142 and defining an internal flow passage 178 having an inlet 177A and an outlet 177B.

The conduit assembly 176 includes a laterally projecting boss 180 defining a receiving cavity 181 for receiving a ribbed anchor portion 184 of a valve member insert 185. The valve member insert 185 includes a transversely oriented, resilient, spring member 186 extending from the lower end of the anchor portion 184. A frusto-conical valve member 187 projects upwardly from the spring member 186. The exterior surface of the valve member 187 is adapted to seal against the conduit outlet 177B. The spring member 186 normally biases the valve member 187 in tight sealing engagement against the conduit outlet end 177B as illustrated in FIG. 7. This defines a one-way valve.

The inlet end of the conduit assembly 176 includes a connector or flange 179 or male thread form, such as is employed in connection systems marketed under the trademark LUER-LOK. This accommodates connection to the second container 148 as described in detail hereinafter. Other suitable conventional or special connecting systems may be employed.

The second container 148 is preferably initially provided with a surrounding, protective sleeve 152 which is removed and discarded subsequent to use.

The second container 148 has a barrel 150 containing a liquid second constituent 146 that is retained within the barrel 150 by a plunger 164 which has a piston 168 slidably disposed within the barrel 150.

The bottom end of the second container 148 defines a discharge end 156. The end 156 includes an outwardly projecting discharge conduit 158 defining an internal discharge passage 159 communicating through the discharge end 156 to accommodate the discharge of fluid from the barrel 150 of the second container 148.

A collar 161 is spaced from, and surrounds, the discharge conduit 158. The collar 161 defines an internal thread form, and this may be of the type that is employed in connection systems marketed under the trademark LUER-LOK. Thus, the collar 161 can be threadingly engaged with the thread form or flange 179 at the inlet end of the connector assembly 176 projecting from the seal 142 in the first container 122. The second container projecting conduit 158 is adapted to enter into the inlet 177A of the conduit assembly 176 and form a leak-tight seal with the conduit 177. The second container collar 161 and conduit 158 thus function as a cooperating connector for connecting the second container 148 to the seal conduit assembly 176. Other suitable connection structures could be used in place of the specific form of the collar 161, conduit 158, and conduit assembly flange 179 illustrated.

Preferably, a secondary, removable closure member 162, in the form of a threaded plug, is threadingly engaged with the collar 161, and it must be removed prior to use. This prevents ingress of contaminants and insures that the liquid second constituent will not leak out of the second container 148. Of course, even if the removable closure 162 is not employed, the liquid second constituent 146 cannot leak out of a small diameter passage 159 because there is no vent system that would admit ambient air into the second container 148 so as to permit the liquid constituent 146 to flow out solely under the influence of gravity. Nevertheless, both containers are preferably held in an inverted position as the second container 148 is inserted into the first container 122 to connect the second container discharge conduit 158 with the first container conduit assembly 176.

The connection process is completed by inserting the second container 148 (with the closure 162 removed) to engage the collar 161 with the flange 179. Then relative rotation between the two containers is effected to complete the threaded engagement.

Subsequently, the first 122 and second 148 containers are moved (i.e., pulled) outwardly relative to each other. As the seal 142 is pulled outwardly, the volume beneath the seal 142 within the first chamber 124 increases and thus lowers the pressure therein. This results in a pressure differential which opens the valve member 187 as the liquid second constituent 146 flows into the first container 122 to combine with the first constituent 140. Ambient air pressure acting on the exterior surface of the plunger piston 168 is transferred to the liquid second constituent 146.

The two containers are pulled outwardly until the bottom interior surface of the plunger piston 168 engages the bottom, interior surface of the second container 148. At this point, all of the liquid second constituent 146 has been expelled from the barrel 150 of the second container 148 into the first container 122. The assembly can be shaken to ensure good mixing.

The first closure 132 can then be removed from the first container 122, and the dispensing end 126 can be connected to a suitable receiving component or discharge tubing (not illustrated). Alternatively, a needle, such as the needle 34 illustrated for the first embodiment in FIG. 5, may be attached to the first container 122.

Subsequently, the plunger 164 and second container 148 can be pushed inwardly to move the seal 142 inwardly further into the first container 122. This expels the combined constituents 140 and 146 from the first container 122.

It will be appreciated that the first container conduit assembly 176 and the second container conduit 158 cooperatively define a coupling or flow-accommodating connection means which permits the liquid second constituent 146 to flow from the second container 148 into the first container 122. This coupling also accommodates the outward movement of the containers 148 and 122 during the transfer of the liquid second constituent from the second container to the first container. Additionally, this coupling accommodates the subsequent inward movement of the containers during the dispensing of the combined constituents from the first container 122.

A third embodiment of the present invention, which includes a modified form of the conduit connector, is illustrated in FIGS. 10 and 10A. This embodiment includes a first container 222 defining a first chamber 24 in which a seal 242 is slidably disposed above a first constituent (not visible in FIGS. 10 and 10A). A conduit 277 is mounted in the seal 242 and extends through the seal 242. The conduit 277 defines an internal passage 78 and has an inlet 277A and an outlet 277B. At the inlet 277A, the conduit 277 includes a thread form or flange 279 which may be identical to the flange 179 described above with reference to the embodiment illustrated in FIGS. 6–9.

The bottom of the seal 242 has a frusto-conical shape 243 with a partial slit 289 oriented transversely to the axis of the frusto-conical shape at a outlet 277B of the conduit 277. This defines a flap or valve member 287 which is attached with an unslit portion 290 (FIG. 10A) to the main body of the seal 242. The portion 290 is resilient and normally biases the valve member 287 upwardly against the outlet 277B of the conduit 277 to occlude the passage 278.

The seal 242 and conduit 277 illustrated in FIGS. 10 and 10A are adapted to cooperate with a second container (not illustrated) that can be identical to the second container 148 described above with reference to the second embodiment illustrated in FIG. 6. The second container can be inserted into the first container 222 and connected to the conduit 277 in the same manner as described above for the connection of the embodiment of the second container 148 with the first container 122 illustrated in FIG. 6. The operation of the embodiment of the system illustrated in FIGS. 10 and 10A with respect to combining the two constituents and subsequently dispensing them is identical with the operation of the second embodiment described above with reference to FIGS. 6–9.

A fourth embodiment, incorporating a presently preferred design, is illustrated in FIGS. 11 and 12. A number of the elements of the fourth embodiment of the syringe system are identical or functionally analogous to corresponding elements in the first embodiment illustrated in FIGS. 15. The elements of the fourth embodiment illustrated in FIGS. 11 and 12 are designated by three digit reference numbers. The last two digits of the fourth embodiment reference numbers for elements corresponding to elements in the first embodiment are identical to the two digit reference numbers used to designate those corresponding elements in the first three embodiments.

With reference to FIG. 11, the preferred form of the syringe system includes a first container 322 which has a first chamber 324 containing a first constituent 340. The lower portion of the first container 322 includes a dispensing end 326 defining a dispensing passage 328. Preferably, the dispensing passage 328 is occluded with a first, removable closure 332 which may be held in a friction fit on the dispensing end 326. Other connection systems may be employed, such as snap-fit beads and grooves, threads, etc.

A moveable seal 342 is provided above the first constituent 340 in the first chamber 324. The seal 342 has a lower end surface defining a conical shape 343. The apex of the cone has at least one slit or preferably two intersecting slits 389 (one of which is visible in FIG. 11). The single slit defines two flaps and the intersecting slits define four flaps 387 which are normally biased to a closed position as illustrated in FIG. 11. The upper end surface of the seal has an enlarged receiving cavity 393 and a smaller entrance passage 394 which together define a retention shoulder 395.

The seal 342 is initially installed in the first container 322 in a frictional engagement sufficient to prevent movement of the seal 342 during transport, storage, and handling. The seal is adapted to be engaged and moved with a second container 348 which includes a barrel 350 sized to be disposed in the first container 322.

The barrel 350 has a discharge end 356 defining a discharge passage 359 communicating through the discharge end 356 to accommodate the discharge of fluid from the barrel 350. The dispensing end 356 has an enlarged head 396 and a smaller neck 398 (FIG. 11). The neck 398 and head 396 together define a transverse shoulder 399.

A liquid second constituent 346 is contained within the barrel 350 below a plunger 364 which has a piston 368. Preferably, in order to minimize the likelihood of contaminant ingress and to minimize the likelihood of leakage of the constituent 346, a suitable closure 362 is removably mounted to the dispensing end 356. The closure 362 may be held on the dispensing end 356 by means of a friction fit or by other suitable conventional or special means, such as threads, snap-fit beads and grooves, etc.

Preferably, a protective sleeve (not illustrated) may be provided for surrounding the barrel 350 in substantially the same manner that the sleeve 52 surrounds the barrel 50 of the second container of the first embodiment illustrated in FIG. 1.

Also, if desired, the first container 322 may include a removable cover (not illustrated), such as the cover 44 shown on the top of the first container 22 of the first embodiment illustrated in FIG. 1.

In order to use the system illustrated in FIGS. 11 and 12, the cap 362 is removed from the second container 348. The second container 348 is then disposed within the first container 322. Preferably, this step is accomplished by first inverting the second container 348 before the closure 362 is removed. The first container 322 is also inverted, and the two containers are telescopically engaged in the inverted position. The second container 348 is pushed into the first container 322 until the second container head 396 sufficiently expands the seal entrance passage 394 and enters into the seal receiving cavity 393. In this position, the second container dispensing end neck 398 is received in the smaller entrance passage 394 which, owing to the resiliency of the seal 342, has assumed its smaller diameter configuration whereby the seal retaining flange 395 engages the second container flange 399. This prevents separation of the second container 348 from the first container seal 342.

In the initially engaged position, wherein the second container dispensing end 356 is connected to the first container seal 342, the seal flaps or valve members 387 remain closed so as to ensure that there will be no leakage of the liquid second constituent into the first constituent 340.

Subsequently, the first and second containers are pulled outwardly relative to each other. Ambient air pressure acting on the plunger 368 results in the liquid second constituent 346 being maintained at ambient atmospheric pressure. The increasing volume of the first chamber 324 under the seal 342 creates a negative pressure differential, and the liquid second constituent 346 forces the valve members 387 outwardly to the open position illustrated in FIG. 12. The liquid second constituent 346 can thus flow into the first constituent 340.

The two containers are pulled outwardly relative to each other until the bottom surface of the plunger piston 368 engages the bottom of the second container barrel 350. At this point, all of the liquid second constituent 346 has been expelled into the first constituent 340 in the first chamber 324. The valve flaps 387 then close. The assembly can then be shaken to ensure good mixing.

Subsequently, the closure 332 is removed from the first container dispensing end 326. The first container dispensing end 326 can then be connected to a receiving component or discharge tubing (not illustrated) or to a needle (such as the needle 34 described above with reference to the first embodiment illustrated in FIGS. 1–5). Then the plunger 364 is pushed inwardly. This urges the plunger piston 368 against the bottom of the second container barrel 350 to move the second container and connected seal 342 toward the bottom of the first container 322. This results in the combined constituents being dispensed from the first container 322.

It will be appreciated that, in all of the embodiments illustrated, the dispensing ends of the first containers are sealed with removable closures (such as the first container dispensing end closure 32.) The second container dispensing end may include a closures (i.e., closure 62 illustrated in FIG. 1). Further, such closures, if employed, may be provided in alternate forms such as threadable elastomeric seal members, flexible adhesive seal members, shrink wrap films, or other closure systems.

Further, after the first and second containers have been initially coupled together and as the containers are subsequently moved (i.e., pushed or pulled) outwardly relative to each other, an inwardly directed force may be applied to the plunger 364 to assist in transferring the second liquid constituent from the second container to the first container.

The above-described syringe system of the present invention provides an advantageous means for dispensing a combination of two constituents that must be kept separate from each other until they are to be used in combination. The system is self-contained and sealed. Reconstitution or dilution of a drug using this system can be effected at bedside when the drug is needed. The choice of the diluent liquid is not restricted or limited because the system accommodates any diluent compatible with the structural materials employed.

The system permits the constituents to be stored in forms in which the stability of the components is maximized. Because the reconstituted product is used immediately, provisions do not have to be made for refrigeration or other storage procedures which might otherwise be required for certain types of reconstituted products.

It will be readily apparent from the foregoing detailed description of the invention and from the illustrations thereof that numerous variations and modifications may be effected without departing from the true spirit and scope of the novel concepts or principles of this invention.

What is claimed is:

1. A syringe system comprising:

a first container including
  a first chamber having a dispensing end defining a dispensing passage communicating through said dispensing end to accommodate the dispensing of fluid from said first chamber,
  a movable seal slidably disposed in said first chamber, and
  a first constituent in said first chamber between said dispensing end and said seal;
a second container including
  a barrel that is sized to be disposed in said first container and that has a discharge end defining a discharge passage communicating through said discharge end to accommodate the discharge of fluid from said barrel,
  a plunger slidably disposed within said barrel, and
  a liquid second constituent in said barrel between said discharge end and said plunger; and
said first container seal and said second container barrel discharge end being engageable to cooperatively define a coupling accommodating the flow of said liquid second constituent from said barrel into said first chamber as said second container and seal move outwardly relative to said first chamber,
wherein said coupling includes:
  (1) said seal is resilient and has at least one slit defining flaps which are biased to a normally closed position and which can open on the downstream side into said first chamber,
  (2) an enlarged receiving cavity in said seal adjacent an upstream side of said flaps and a smaller entrance passage in said seal opening to said cavity whereby a retention shoulder is defined at one end of said cavity around said smaller entrance passage, and
  (3) an enlarged head at said second container barrel discharge end for being received in said seal enlarged receiving cavity and a smaller neck at said second container barrel discharge end for being received in said seal entrance passage whereby said second container barrel discharge passage is normally occluded by said seal flaps in the biased closed position.

2. The system in accordance with claim 1 in which said plunger includes a piston and a shank removably mounted in said piston.

3. The system in accordance with claim 1 in which said coupling includes:
  (1) a hollow piercing needle carried at said barrel discharge end in communication with said discharge passage, and
  (2) a portion of said seal being fully penetratable by said piercing needle.

4. The system in accordance with claim 1 in which said coupling includes:
  (1) a conduit extending through said seal and having inlet and outlet ends,
  (2) a flapper valve member in said seal adjacent said conduit outlet end and biased to a normally closed position occluding said conduit outlet end,
  (3) a flange on said conduit inlet end, and
  (4) a thread form on said second container barrel discharge end for threadingly engaging said flange whereby communication is established between said discharge end and said conduit.

5. The system in accordance with claim 1 further including
  a first removable closure occluding said dispensing passage;
  a second removable closure occluding said barrel discharge passage; and
  a cover removably mounted to said first container opposite said dispensing end.

6. The system in accordance with claim 1 further including a hollow needle mounted on said dispensing end of said first container in communication with said dispensing passage.

7. The system in accordance with claim 1 further including a protective sleeve for receiving said second container in a storage mode.

8. The system in accordance with claim 1 in which said seal is a resilient elastomeric material.

9. A prefilled syringe system for separately storing a first constituent and a liquid second constituent and for subsequently mixing and dispensing a mixture of said constituents, said system comprising:
a first container including
  a first chamber having a dispensing end defining a dispensing passage communicating through said dispensing end to accommodate the dispensing of fluid from said first chamber,
  a first removable closure sealingly occluding said dispensing passage,
  a movable seal slidably disposed in said first chamber, and
  a first constituent in said first chamber between said dispensing end and said seal;
a second container including
  a barrel that is sized to be disposed in said first container and that has a discharge end defining a discharge passage communicating through said discharge end to accommodate the discharge of fluid from said barrel,
  a second removable closure occluding said barrel discharge passage,
  a plunger slidably disposed within said barrel, and
  a liquid second constituent in said barrel between said discharge end and said plunger; and
said first container seal and said second container barrel discharge end being engageable upon removal of said second closure to cooperatively define a coupling accommodating the flow of said liquid second constituent from said barrel into said first chamber as said second container and seal move outwardly relative to said first chamber, and said plunger being axially engageable with said barrel to move said barrel and seal inwardly relative to said first chamber to expel the combined contents of said first chamber,
wherein said coupling includes:
  (1) said seal is resilient and has at least one slit defining flaps which are biased to a normally closed position and which can open on the downstream side into said first chamber,
  (2) an enlarged receiving cavity in said seal adjacent an upstream side of said flaps and a smaller entrance passage in said seal opening to said cavity whereby a retention shoulder is defined at one end of said cavity around said smaller entrance passage, and
  (3) an enlarged head at said second container barrel discharge end for being received in said seal enlarged receiving cavity upon removal of said second closure and a smaller neck at said second container barrel discharge end for being received in said seal entrance passage whereby said second container barrel discharge passage is normally occluded by said seal flaps in the biased closed position.

10. The system in accordance with claim 9 in which said plunger includes a piston and a shank removably mounted in said piston.

11. The system in accordance with claim 9 in which said coupling includes:
   (1) a hollow piercing needle carried at said barrel discharge end in communication with said discharge passage, and
   (2) a portion of said seal being fully penetratable by, and couplingly engaging, said piercing needle upon removal of said second closure from said barrel discharge end.

12. The system in accordance with claim 9 in which said coupling includes
   (1) a conduit extending through said seal and having inlet and outlet ends,
   (2) a valve member in said seal adjacent said conduit outlet end and biased to a normally closed position occluding said conduit outlet end,
   (3) a connector on said conduit inlet end, and
   (4) a cooperating connector on said second container barrel discharge end for engaging said conduit inlet end connector upon removal of said second closure whereby communication is established between said discharge end and said conduit.

13. The system in accordance with claim 12 wherein the connector on said conduit inlet end includes a threadable flange and the cooperating connector on said second container barrel discharge end includes a threaded form for threadingly engaging the threadable flange.

14. The system in accordance with claim 9 further including a hollow needle mounted on said dispensing end of said first container in communication with said dispensing passage.

15. A syringe system comprising:
   a first container including
      a first chamber having a dispensing end defining a dispensing passage communicating through said dispensing end to accommodate the dispensing of fluid from said first chamber,
      a movable seal slidably disposed in said first chamber, and
      a first constituent in said first chamber between said dispensing end and said seal;
   a second container including
      a barrel that is sized to be disposed in said first container and that has a discharge end defining a discharge passage communicating through said discharge end to accommodate the discharge of fluid from said barrel,
      a plunger slidably disposed within said barrel, and
      a liquid second constituent in said barrel between said discharge end and said plunger; and
   said first container seal and second container barrel discharge end including means for being coupled together to accommodate the flow of said liquid second constituent from said barrel into said first chamber as said second container and seal move outwardly relative to said first chamber,
   wherein said means for being coupled together includes
      (1) said seal is resilient and has at least one slit defining flaps which are biased to a normally closed position and which can open on the downstream side into said first chamber,
      (2) an enlarged receiving cavity in said seal adjacent an upstream side of said flaps and a smaller entrance passage in said seal opening to said cavity whereby a retention shoulder is defined at one end of said cavity around said smaller entrance passage, and
      (3) an enlarged head at said second container barrel discharge end for being received in said seal enlarged receiving cavity and a smaller neck at said second container barrel discharge end for being received in said seal entrance passage whereby said second container barrel discharge passage is normally occluded by said seal flaps in the biased closed position.

16. The system in accordance with claim 15 in which said means for being coupled together includes
   (1) a conduit extending through said seal and having inlet and outlet ends,
   (2) a flapper valve member in said seal adjacent said conduit outlet end and biased to a normally closed position occluding said conduit outlet end,
   (3) a flange on said conduit inlet end, and
   (4) a thread form on said second container barrel discharge end for threadingly engaging said flange whereby communication is established between said discharge end and said conduit.

17. The system in accordance with claim 15 in which said means for being coupled together includes:
   (1) a hollow piercing needle carried at said barrel discharge end in communication with said discharge passage, and
   (2) a portion of said seal being fully penetratable by, and couplingly engaging, said piercing needle.

18. A syringe system comprising:
   a first container including
      a first chamber having a dispensing end defining a dispensing passage communicating through said dispensing end to accommodate the dispensing of fluid from said first chamber,
      a movable seal slidably disposed in said first chamber whereby a first constituent can be disposed in said first chamber between said dispensing end and said seal;
   a second container including
      a barrel that is sized to be disposed in said first container and that has a discharge end defining a discharge passage communicating through said discharge end to accommodate the discharge of fluid from said barrel,
      a plunger slidably disposed within said barrel whereby a liquid second constituent can be disposed in said barrel between said discharge end and said plunger; and
   said first container seal and second container barrel discharge end including means for being coupled together to accommodate the flow of said liquid second constituent from said barrel into said first chamber as said second container and seal move outwardly relative to said first chamber,
   wherein said means for being coupled together includes
      (1) said seal is resilient and has at least one slit defining flaps which are biased to a normally closed position and which can open on the downstream side into said first chamber,
      (2) an enlarged receiving cavity in said seal adjacent an upstream side of said flaps and a smaller entrance passage in said seal opening to said cavity whereby a retention shoulder is defined at one end of said cavity around said smaller entrance passage, and (3) an enlarged head at said second container barrel discharge end for being received in said seal enlarged receiving cavity and a smaller neck at said second container barrel discharge end for being received in said seal entrance passage whereby said second container barrel discharge passage is normally occluded by said seal flaps in the biased closed position.

* * * * *